(12) United States Patent
Huang et al.

(10) Patent No.: US 12,017,115 B2
(45) Date of Patent: Jun. 25, 2024

(54) METHOD FOR BUILDING UP AN ENERGY METABOLISM SYSTEM FOR MONITORING EXERCISE

(71) Applicant: bOMDIC, Inc., New Taipei (TW)

(72) Inventors: Tai-Yu Huang, New Taipei (TW); Chien-Yu Chiu, New Taipei (TW); Liang-Yi Lee, New Taipei (TW)

(73) Assignee: BOMDIC INC., New Taipei (TW)

(*) Notice: Subject to any disclaimer, the term of this patent is extended or adjusted under 35 U.S.C. 154(b) by 833 days.

(21) Appl. No.: 17/070,947

(22) Filed: Oct. 15, 2020

(65) Prior Publication Data
US 2022/0111255 A1   Apr. 14, 2022

Related U.S. Application Data

(63) Continuation-in-part of application No. 17/070,040, filed on Oct. 14, 2020, now abandoned.

(51) Int. Cl.
*A63B 24/00* (2006.01)
*A61B 5/00* (2006.01)
(Continued)

(52) U.S. Cl.
CPC .......... *A63B 24/0062* (2013.01); *A61B 5/026* (2013.01); *A61B 5/1118* (2013.01);
(Continued)

(58) Field of Classification Search
CPC . A63B 24/0062; A61B 5/1118; A61B 5/4519; A61B 5/4866; A61B 5/7267;
(Continued)

(56) References Cited

U.S. PATENT DOCUMENTS

2008/0119763 A1* 5/2008 Wiener ................ A61B 5/224
600/587
2014/0074407 A1* 3/2014 Hernandez-Silveira ...................
A61B 5/4866
600/521
(Continued)

FOREIGN PATENT DOCUMENTS

GB   2505690 A  *  3/2014  ............. A61B 5/083
WO   WO-2011060780 A2  *  5/2011  ............... A61B 5/22

OTHER PUBLICATIONS

Umberger, Brian R., Karin GM Gerritsen, and Philip E. Martin. "Muscle fiber type effects on energetically optimal cadences in cycling." Journal of biomechanics 39.8 (2006): 1472-1479. (Year: 2006).*

*Primary Examiner* — Jesse P Frumkin
(74) *Attorney, Agent, or Firm* — Chieh-Mei Wang

(57) ABSTRACT

The present invention discloses a method for monitoring an exercise. The method comprises: building up an energy metabolism system having an energy metabolism feature, wherein the energy metabolism feature comprises a first feature factor, wherein the first feature factor is associated with a first biological system being one of a plurality of biological systems of a human body and not associated with the complete human body; building up a mathematical model describing that an energy expenditure depends on at least one exercise-associated parameter based on the energy metabolism feature for the energy metabolism system; estimating the energy expenditure based on the at least one exercise-associated parameter measured in the exercise by the mathematical model of the energy metabolism system; and monitoring the exercise based on the energy expenditure.

18 Claims, 6 Drawing Sheets

(51) Int. Cl.
*A61B 5/026* (2006.01)
*A61B 5/11* (2006.01)

(52) U.S. Cl.
CPC .... *A61B 5/4866* (2013.01); *A63B 2024/0065* (2013.01); *A63B 2024/0068* (2013.01)

(58) Field of Classification Search
CPC ....... A61B 5/0205; A61B 5/389; A61B 5/024; A61B 5/7264; G16H 20/30; G16H 50/50
See application file for complete search history.

(56) References Cited

U.S. PATENT DOCUMENTS

2019/0080802 A1\* 3/2019 Ziobro ................... G16H 20/30
2023/0129375 A1\* 4/2023 Huijbregts ............. A61B 5/222
600/483

\* cited by examiner

200

201
Build up an energy metabolism system having an energy metabolism feature, wherein the energy metabolism feature comprises a first feature factor, wherein the first feature factor is associated with a first biological system being one of a plurality of biological systems of a human body and not associated with the complete human body.

202
Build up a mathematical model describing that an energy expenditure depends on at least one exercise-associated parameter based on the energy metabolism feature for the energy metabolism system.

203
Estimate the energy expenditure based on the at least one exercise-associated parameter measured in the exercise by the mathematical model of the energy metabolism system.

204
Monitoring the exercise based on the energy expenditure.

FIG. 2

METHOD FOR BUILDING UP AN ENERGY METABOLISM SYSTEM FOR MONITORING EXERCISE

CROSS-REFERENCE TO RELATED APPLICATION

This application is a continuation-in-part of U.S. patent application Ser. No. 17/070,040 filed on Oct. 14, 2020, which is incorporated by reference herein in its entirety.

BACKGROUND OF THE INVENTION

1. Field of the Invention

The present invention relates to a method for monitoring an exercise, and more particularly to a method for monitoring an exercise by building up an energy metabolism system.

2. Description of Related Art

A combination of many factors must be taken into account in evaluating the exercise condition. The factors may come from the interior of the body or the external environment. Therefore, how to use the limited computer resource (e.g., energy metabolism system) to precisely evaluate exercise condition is very hard.

Conventionally, aerobic energy metabolism system and anaerobic energy metabolism system are both used in the algorithm for evaluating the exercise condition (e.g., stamina, training load, fatigue or recovery). Each of aerobic energy metabolism system and anaerobic energy metabolism system takes all of the biological systems of the human body into account together. In other words, both aerobic energy metabolism and anaerobic energy metabolism happen in each of the biological systems of the human body. However, there is much difference in the degree of exercise response among the biological systems of the human body. That is, both aerobic energy metabolism system and anaerobic energy metabolism system take a portion of biological systems of the lower degree of exercise response of the human body into account. Therefore, it is still imperfect that aerobic energy metabolism system and anaerobic energy metabolism system are both used for evaluating the exercise condition.

Physiologically, the energy metabolism above the anaerobic threshold is more complicated than the energy metabolism below the anaerobic threshold. Therefore, how to use the limited computer resources (e.g., energy metabolism system) to precisely evaluate exercise condition is the most important when the exercise intensity is above a threshold, especially the threshold of the exercise intensity is an anaerobic threshold.

Besides, the anaerobic threshold is not a constant and varies with many factors coming from the interior of the body or the external environment. Therefore, how to use the limited computer resources to finish the algorithm of the energy metabolism system to make sure that the energy metabolism system is operated above the anaerobic threshold is also the most important.

Further, the user can't take exercise with higher exercise intensity (e.g., above anaerobic threshold) for a long time and the user may reduce the exercise intensity for recovery in a first short time and raise the exercise intensity for exercise in a second short time intermittently. If the algorithm of the energy metabolism system takes a portion of biological systems of the lower degree of the exercise response of the human body, it is hard to use the algorithm of the energy metabolism system to precisely monitor the variation of the exercise intensity in each of the first short time and the second short time during the intermittent exercise session because the variation rate of the exercise intensity is larger and the variation frequency of the exercise intensity is larger during the intermittent exercise session.

Accordingly, the present invention proposes a method for monitoring an exercise by building up an energy metabolism system to overcome the above-mentioned disadvantages.

SUMMARY OF THE INVENTION

The present invention builds up a mathematical model based on the energy metabolism feature for the energy metabolism system. The energy metabolism feature comprises a first feature factor associated with associated with a first biological system being one of a plurality of biological systems of a human body and not associated with the complete human body. The first biological system may be an exercise-responsive system having a degree of exercise response more than a threshold. The threshold is more than the minimum of the degree of exercise response. The parameter of the degree of exercise response may be a ratio of a first blood flow rate in the heavy exercise to a second blood flow rate at rest. The ratio may more than 1.1. The heavy exercise may be a maximal exercise with the oxygen consumption being 100% $VO_{2max}$. The biological system may be a muscular system. The biological system may be a skeletal muscle system which is one sub-system of the muscular system. In other words, the present invention builds up a mathematical model partially or completely based on one biological system of the higher degree of exercise response of the human body and not based on one biological system of the lower degree of exercise response of the human body for the energy metabolism system. Further, the present invention builds up a mathematical model based on the elite biological system of the human body; therefore, the present invention can evaluate the exercise condition more precisely.

Besides the above description, the first feature factor is expressed above the first threshold of the exercise intensity such that the energy metabolism system is operated above the first threshold of the exercise intensity (e.g., anaerobic threshold) or the energy metabolism feature may further comprise a second feature factor expressed above the second threshold of the exercise intensity more than the first threshold of the exercise intensity such that the energy metabolism system is operated above the second threshold of the exercise intensity (e.g., anaerobic threshold). Further, the present invention builds up a mathematical model based on the elite biological system of the human body associated with the exercise intensity above a threshold (e.g., anaerobic threshold) for the energy metabolism system; therefore, the present invention can use the limited/the least energy metabolism system(s) to precisely evaluate the exercise condition with the exercise intensity more than a threshold in the most efficient and the most economical way when facing the complicated human physiological environment above the threshold of the exercise intensity (e.g., anaerobic threshold).

More preferably, if the first feature factor is expressed above the first threshold of the exercise intensity such that the energy metabolism system is operated above the first threshold of the exercise intensity, the present invention builds up a mathematical model based on the elite biological system of the human body and the exercise intensity above the first threshold (e.g., anaerobic threshold) both existing in the first feature factor for the energy metabolism system; therefore, the present invention can use the limited/the least feature factor(s) to build up a mathematical model (i.e. save computer resource: the number of the feature factors is less>> the computer program code isn't more complicated>> save more computer resource) in the limited/the least energy metabolism system(s) to precisely evaluate the exercise condition with the exercise intensity more than the first threshold in the most efficient and the most economical way when facing the complicated human physiological environment above the first threshold of the exercise intensity (e.g., anaerobic threshold).

By the algorithm implemented in the computer of the present invention, the computer of the present invention performs operations described in claims or the following descriptions to building up an energy metabolism system to monitoring an exercise.

In one embodiment, the present invention discloses a method for monitoring an exercise. The method comprises: building up an energy metabolism system having an energy metabolism feature, wherein the energy metabolism feature comprises a first feature factor, wherein the first feature factor is associated with a first biological system being one of a plurality of biological systems of a human body and not associated with the complete human body; building up a mathematical model describing that an energy expenditure depends on at least one exercise-associated parameter based on the energy metabolism feature for the energy metabolism system; estimating the energy expenditure based on the at least one exercise-associated parameter measured in the exercise by the mathematical model of the energy metabolism system; and monitoring the exercise based on the energy expenditure.

In one embodiment, the present invention discloses a method for monitoring an exercise. The method comprises: building up an first energy metabolism system having an first energy metabolism feature, wherein the first energy metabolism system is operated above a first threshold of an exercise intensity, wherein the first energy metabolism feature comprises a first feature factor, wherein the first feature factor is associated with a first biological system being one of a plurality of biological systems of a human body and not associated with the complete human body; building up a first mathematical model describing that a first energy expenditure depends on at least one exercise-associated parameter based on the first energy metabolism feature for the first energy metabolism system; building up an second energy metabolism system having an second energy metabolism feature, wherein the second energy metabolism system is operated above a second threshold of the exercise intensity, wherein the first threshold of the exercise intensity is larger than the second threshold of the exercise intensity; building up a second mathematical model describing that a second energy expenditure depends on the at least one exercise-associated parameter based on the second energy metabolism feature for the second energy metabolism system; estimating the first energy expenditure and the second energy expenditure based on the at least one exercise-associated parameter measured in the exercise respectively by the first mathematical model of the first energy metabolism system and the second mathematical model of the first energy metabolism system; and monitoring the exercise based on the first energy expenditure and the second energy expenditure.

In one embodiment, the present invention discloses a method for monitoring an exercise. The method comprises: building up an energy metabolism system having an energy metabolism feature, wherein the energy metabolism feature comprises a first feature factor, wherein the first feature factor is associated with a first biological system being one of a plurality of biological systems of a human body and not associated with the complete human body, wherein the first biological system is an exercise-responsive system having a ratio of a first blood flow rate in the heavy exercise to a second blood flow rate at rest, wherein the ratio is more than 3, wherein the first feature factor is expressed above an anaerobic threshold such that the energy metabolism system is capable of being operated above the anaerobic threshold without a second feature factor being combined with the first feature factor in the energy metabolism feature; building up a mathematical model describing that an energy expenditure depends on at least one exercise-associated parameter based on the energy metabolism feature for the energy metabolism system; estimating the energy expenditure based on the at least one exercise-associated parameter measured in the exercise by the mathematical model of the energy metabolism system, wherein the at least one exercise-associated parameter comprises an exercise intensity measured by a sensor; and monitoring the exercise based on the energy expenditure.

The detailed technology and above preferred embodiments implemented for the present invention are described in the following paragraphs accompanying the appended drawings for people skilled in the art to well appreciate the features of the claimed invention.

BRIEF DESCRIPTION OF THE DRAWINGS

The foregoing aspects and many of the accompanying advantages of this invention will become more readily appreciated as the same becomes better understood by reference to the following detailed description when taken in conjunction with the accompanying drawings, wherein:

FIG. 2 illustrates a method for building up an energy metabolism system to monitoring an exercise;

DETAILED DESCRIPTION OF THE ILLUSTRATED EMBODIMENTS

Figure 1:
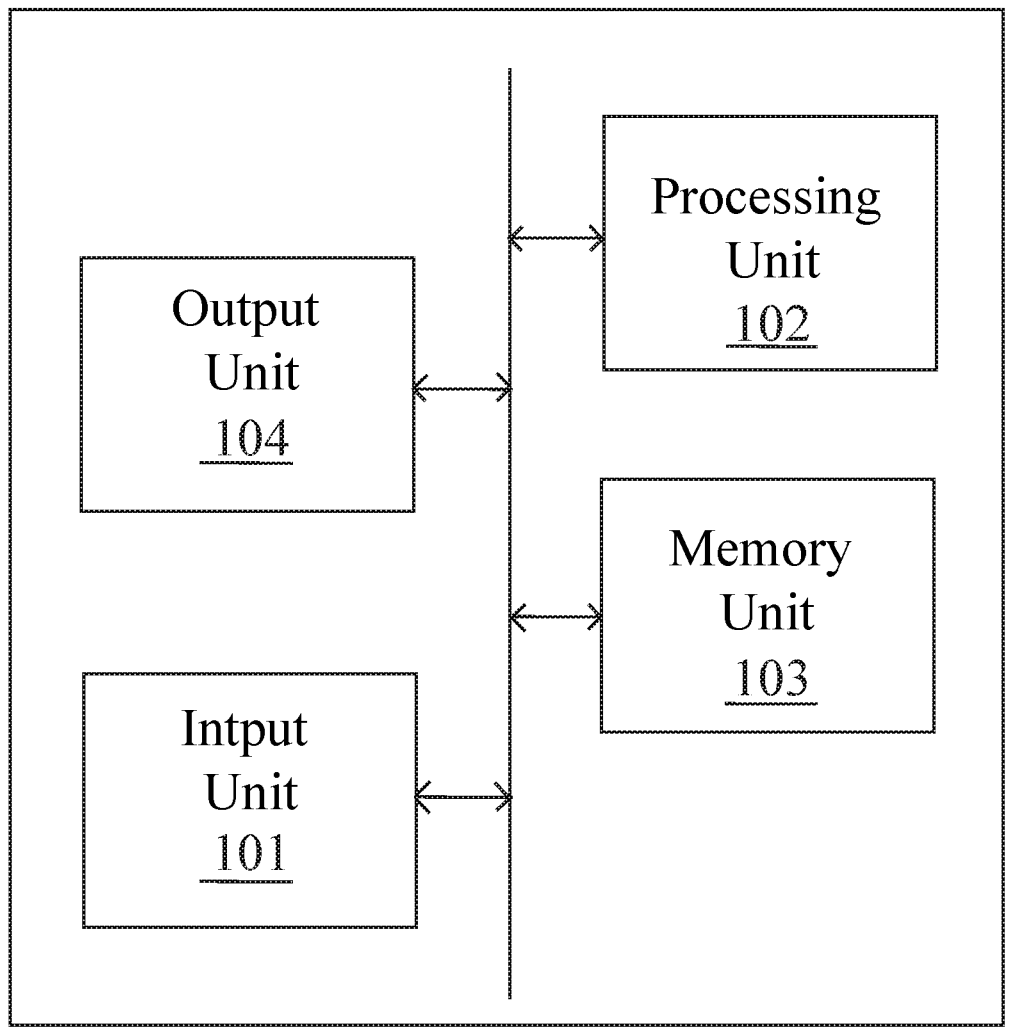
FIG. 1 illustrates a schematic block diagram of an exemplary apparatus in the present invention.

The detailed explanation of the present invention is described as following. The described preferred embodiments are presented for purposes of illustrations and description and they are not intended to limit the scope of the present invention.

Definition of the Terms

Feature Factor

The energy metabolism feature of the energy metabolism system may comprise at least one feature factor. The feature factor $S_i$ may be associated with the complete human body. The terminology "associated with the complete human body" means that "the energy metabolism exists in each cell or each biological system of the complete human body, but the degree of energy metabolism reaction of each cell or each biological system of the complete human body may be different based on a given physiological condition." The feature factor $S_1$ may be associated with whether the oxygen consumption is needed in the energy metabolism or not. For example, the feature factor $S_{11}$ may be associated with an aerobic energy metabolism and the feature factor $S_{12}$ may be associated with an anaerobic energy metabolism expressed above (about) the anaerobic threshold. The feature factor $S_2$ may be associated with the energy metabolism source. For example, the feature factor $S_{21}$ may be associated with the energy metabolism of the carbohydrate, the feature factor $S_{22}$ may be associated with the energy metabolism of the fat and the feature factor $S_{23}$ may be associated with the energy metabolism of the protein. The feature factor $F_i$ may be associated with a first biological system being one of a plurality of biological systems of a human body and not associated with the complete human body. The terminology "associated with a first biological system BS1 being one of a plurality of biological systems of a human body and not associated with the complete human body" means that "the feature factor $F_i$ exists in one biological system BS1 of the human body but doesn't exist in any other biological system BS2 of the human body." In one embodiment, the biological system BS1 may be a skeletal muscle system which is one sub-system of the muscular system (The skeletal muscle system has two types: slow-twitch muscle fibers and fast-twitch muscle fibers; slow-twitch muscle fibers have one type: type I muscle fibers, and fast-twitch muscle fibers have two types: type IIa muscle fibers and type IIx muscle fibers). The feature factor $F_1$ may be associated with one biological system BS1 responding to the exercise-associated parameter (e.g., exercise intensity or exercise time). The feature factor $F_{11}$ may be associated with type I muscle fibers responding to the exercise-associated parameter, the feature factor $F_{12}$ may be associated with type IIa muscle fiber responding to the exercise-associated parameter and the feature factor $F_{13}$ may be associated with type IIx muscle fiber responding to the exercise-associated parameter. However, the present invention is not limited to this case.

The Degree of Active Participation Associated with the Biological System

The degree of active participation associated with the biological system of the human body is a parameter used for evaluating whether the energy metabolism of the biological system of the human body is thriving or not. The degree of active participation associated with the biological system may be the degree of active participation of a component of the biological system. The degree of active participation may be presented in any suitable form. For example, the biological system has 100 cells, 80 cells are active, 20 cells are inactive, the degree of active participation is 80% if the degree of active participation is presented in the form of a ratio of the number of the active cells in the biological system to the number of the total cells in the biological system; the degree of active participation is 4 if the degree of active participation is presented in the form of a ratio of the number of the active cells in the biological system to the number of the inactive cells in the biological system. For how to distinguish the word "active" from the word "inactive", an active threshold may be defined such that the it is called "active" above the active threshold and it is called "inactive" below the active threshold. The active threshold may be fixed or variable.

Exercise Intensity

The exercise intensity may refer to how much energy is expended when exercising. The exercise intensity may define how hard the body has to work to overcome a task/exercise. Exercise intensity may be measured in the form of the internal workload. The parameter of the exercise intensity associated with the internal workload may be associated with a heart rate, an oxygen consumption, a pulse, a respiration rate and RPE (rating perceived exertion). The exercise intensity may be measured in the form of the external workload. The parameter of the exercise intensity associated with the external workload may be associated with a speed, a power, a force, a motion intensity, an energy expenditure rate, a motion cadence or other kinetic data created by the external workload resulting in energy expenditure. The heart rate may be often used as a parameter of the exercise intensity.

The method in the present invention can be applied in all kinds of apparatuses, such as an exercise measurement system, a wrist top device, a mobile device, a server or a combination of at least one of the exercise measurement system, the wrist top device, the mobile device and the server. FIG. 1 illustrates a schematic block diagram of an exemplary apparatus 100 in the present invention. The apparatus 100 may comprise an input unit 101, a processing unit 102, a memory unit 103 and an output unit 104. The input unit 101 may comprise a first sensor which may measure the exercise intensity associated with the physiological data, the cardiovascular data or the internal workload from the user's body. The exercise intensity may be measured by applying a skin contact from chest, wrist or any other human part. Preferably, the exercise intensity is a heart rate and the sensor is a heart rate senor. The input unit 101 may comprise a second sensor (e.g., motion sensor) which may measure the exercise intensity associated with the external workload. The second sensor may comprise at least one of an accelerometer, a magnetometer and a gyroscope. The input unit 101 may further comprise a position sensor (e.g., GPS: Global Positioning System). The processing unit 102 may be any suitable processing device for executing software instructions, such as a central processing unit (CPU). The memory unit 103 may include random access memory (RAM) and read only memory (ROM), but it is not limited to this case. The memory unit 103 may include any suitable non-transitory computer readable medium, such as ROM, CD-ROM, DVD-ROM and so on. Also, the non-transitory computer readable medium is a tangible medium. The non-transitory computer readable medium includes a computer program code which, when executed by the processing unit 102, causes cause the apparatus 100 to perform desired operations (e.g., operations listed in claims). The output unit 104 may be a display for displaying exercise guiding, exercise scheme or exercise index. The displaying mode may be in the form of words, a voice or an image.

Figure 3:
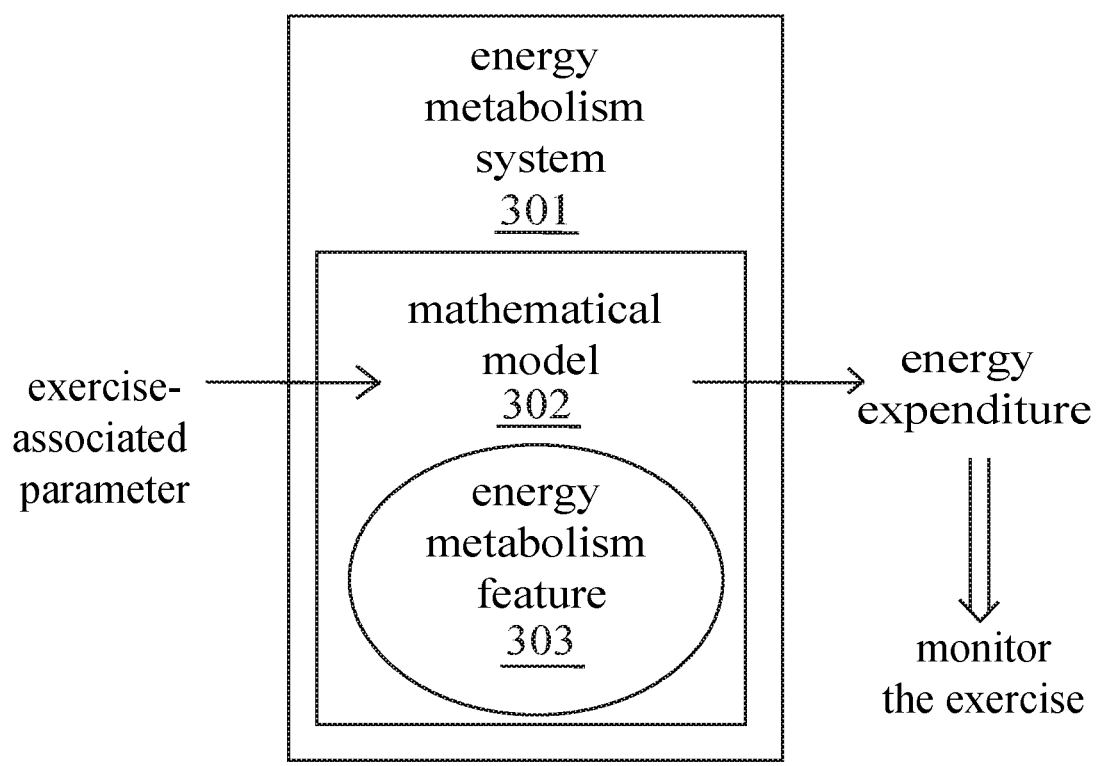
FIG. 3 illustrates a schematic block diagram for building up an energy metabolism system to monitor an exercise in FIG. 2.

FIG. 2 illustrates a method 200 for building up an energy metabolism system 301 to monitoring an exercise. FIG. 3 illustrates a schematic block diagram 300 for building up an energy metabolism system 301 to monitor an exercise in FIG. 2. The process in FIG. 2 starts in step 201: building up an energy metabolism system 301 having an energy metabolism feature 303 (by the processing unit 102), wherein the energy metabolism feature 303 comprises a first feature factor $F_i$, wherein the first feature factor is associated with a first biological system being one of a plurality of biological systems of a human body and not associated with the complete human body. The human body is composed of many biological systems, such as muscular system, respiratory system, digestive system, cardiovascular system, skeletal system and nervous system. The first biological system may be one of muscular system, respiratory system, digestive system, cardiovascular system, skeletal system and nervous system. The first biological system may be an exercise-responsive system having a degree of exercise response more than a threshold. The threshold is more than the minimum of the degree of exercise response. The parameter of the degree of exercise response may be a ratio of a first blood flow rate in the heavy exercise to a second blood flow rate at rest. The ratio may be more than 1.1. The ratio may be more than 1.2. The ratio may be more than 1.5. The ratio may be more than 2. The ratio may more than 3. The ratio may be more than 4. The ratio may be more than 5. The ratio may be more than 8. The ratio may be more than 10. The ratio may be more than 13. The ratio may be more than 16. The ratio may be more than 19. The heavy exercise may be a maximal exercise with the oxygen consumption being 100% $VO_{2max}$. The first biological system may be a muscular system. The first biological system may be a skeletal muscle system which is one sub-system of the muscular system. In other words, the present invention builds up a mathematical model 302 (described below) partially or completely based on one biological system of the higher degree of exercise response of the human body and not based on one biological system of the lower degree of exercise response of the human body for the energy metabolism system. Further, the present invention builds up a mathematical model 302 based on the elite biological system of the human body; therefore, the present invention can evaluate the exercise condition more precisely.

For convenience of description, the exemplary biological system is a skeletal muscle system in the following; however, the present invention is not limited to this case.

In step 202: building up a mathematical model 302 describing that an energy expenditure depends on at least one exercise-associated parameter based on the energy metabolism feature 303 for the energy metabolism system 301 (by the processing unit 102). The exercise-associated parameter(s) may comprise at least one of an exercise intensity and an exercise time. The exercise-associated parameter(s) may comprise an exercise intensity.

The energy metabolism feature 303 may comprise at least one feature factor. The feature factor has been defined above. Once at least one feature factor of the energy metabolism feature 303 is determined, the mathematical model 302 can be built up based on at least one feature factor of the energy metabolism feature 303 for the energy metabolism system 301. If the energy metabolism feature 303 has at least two feature factors, the mathematical model 302 can be built up based on a combination of at least two feature factors of the energy metabolism feature 303 for the energy metabolism system 301.

The energy metabolism feature 303 of the energy metabolism system 301 may comprise only one feature factor and the only one feature factor is a feature factor $F_1$. For example, if the only one feature factor $F_i$ is associated with type I muscle fibers, the energy metabolism system 301 can be abbreviated as I system in the present invention. The mathematical model 302 of I system describes that the energy expenditure depends on at least one exercise-associated parameter based on the energy metabolism feature 303 of type I muscle fibers. For example, if the only one feature factor $F_i$ is associated with type IIa muscle fibers, the energy metabolism system 301 can be abbreviated as IIa system in the present invention. The mathematical model 302 of IIa system describes that the energy expenditure depends on at least one exercise-associated parameter based on the energy metabolism feature 303 of type IIa muscle fibers. For example, if the only one feature factor $F_i$ is associated with type IIx muscle fibers, the energy metabolism system 301 can be abbreviated as IIx system in the present invention. The mathematical model 302 of IIx system describes that the energy expenditure depends on at least one exercise-associated parameter based on the energy metabolism feature 303 of type IIx muscle fibers.

The energy metabolism feature 303 of the energy metabolism system 301 may comprise at least two feature factors. One of at least two feature factors is a feature factor $F_i$; another of at least two feature factors may a feature factor $F_j$ or may be a feature factor $S_i$. The mathematical model 302 can be built up based on a combination of at least two feature factors of the energy metabolism feature 303 for the energy metabolism system 301.

In one embodiment, the energy metabolism feature 303 of the energy metabolism system 301 may comprise two feature factors, one is a feature factor $F_i$ and the other is a feature factor $S_i$. For example, if one is associated with type IIa muscle fibers and the other is associated with the carbohydrate, the energy metabolism system 301 can be abbreviated as IIa-CHO system in the present invention. The mathematical model 302 of IIa-CHO system describes that the energy expenditure depends on at least one exercise-associated parameter based on the energy metabolism feature 303 of the carbohydrate associated with type IIa muscle fibers. The energy metabolism feature 303 of the carbohydrate associated with type IIa muscle fibers may be aerobic or anaerobic.

In another embodiment, the energy metabolism feature 303 of the energy metabolism system 301 may comprise three feature factors, one of three feature factors is a feature factor $F_i$, and the others of three feature factors are feature factors $S_i$. For example, if one of three feature factors is associated with type IIa muscle fibers, one of three feature factors is associated with the aerobic energy metabolism and one of three feature factors is associated with the carbohydrate, the energy metabolism system 301 can be abbreviated as IIa-CHO-aerobic system in the present invention. The mathematical model 302 of IIa-CHO-aerobic system describes that the energy expenditure depends on at least one exercise-associated parameter based on the aerobic energy metabolism feature of the carbohydrate associated with type IIa muscle fibers.

It should be noted that if each feature factor of N feature factors (N is integer and at least two) is expressed above the threshold $EI_i$ (i=1, 2, . . . , N) of the exercise intensity, the energy metabolism system 301 is operated above the threshold which is the maximum of the threshold $EI_i$, the threshold $EI_2$ . . . and the threshold $EI_N$ after the mathematical model 302 is built up based on a combination of N feature factors of the energy metabolism feature 303 for the energy metabolism system 301.

Figure 4A:
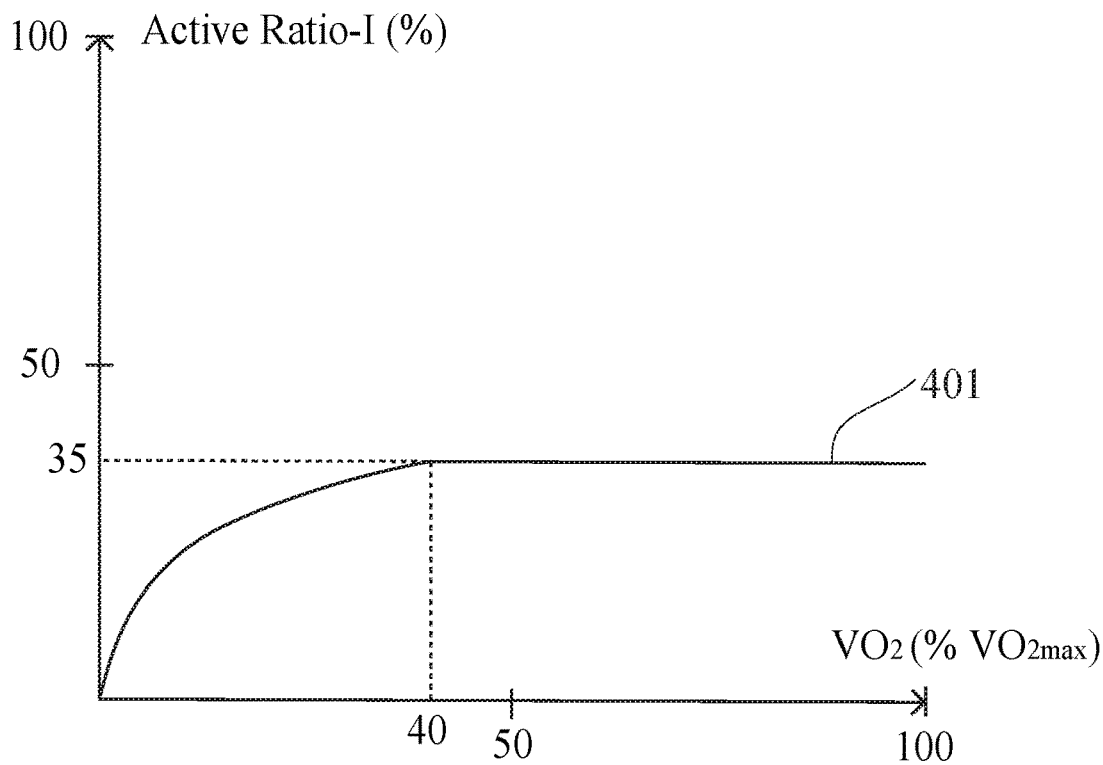
FIG. 4A illustrates the relationship between the degree of active participation AP1 of type I muscle fibers and the exercise intensity.
Figure 4B:
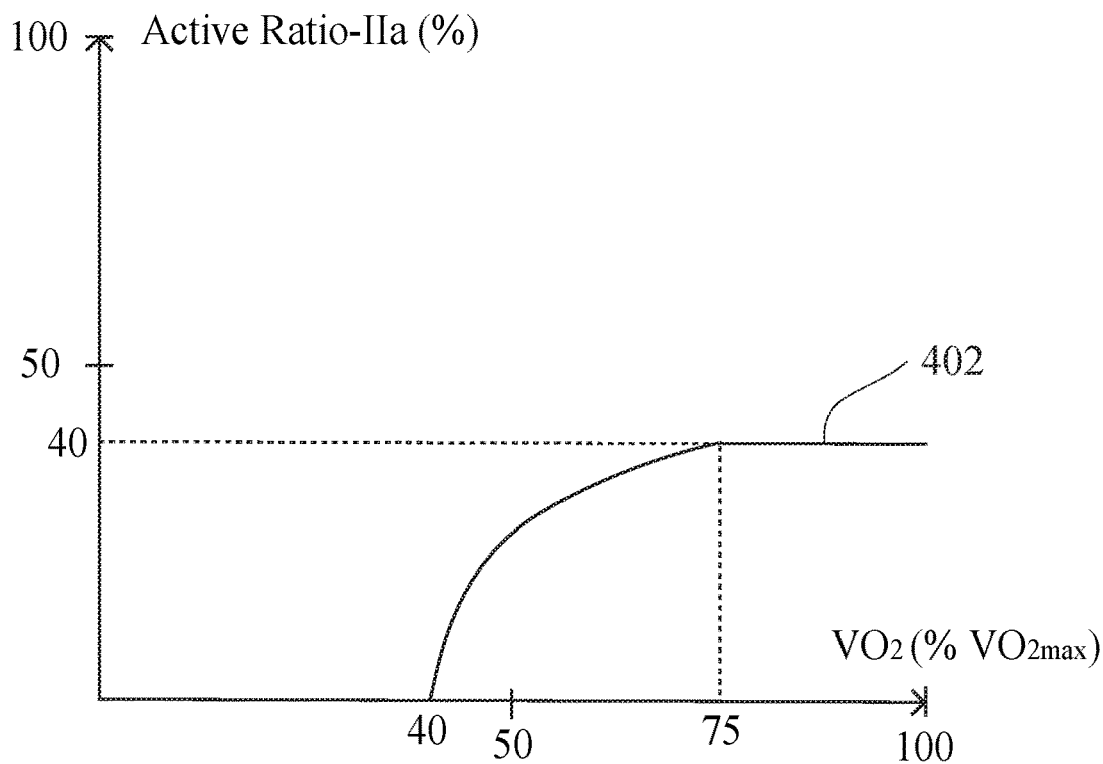
FIG. 4B illustrates the relationship between the degree of active participation AP2 of type IIa muscle fibers and the exercise intensity.
Figure 4C:
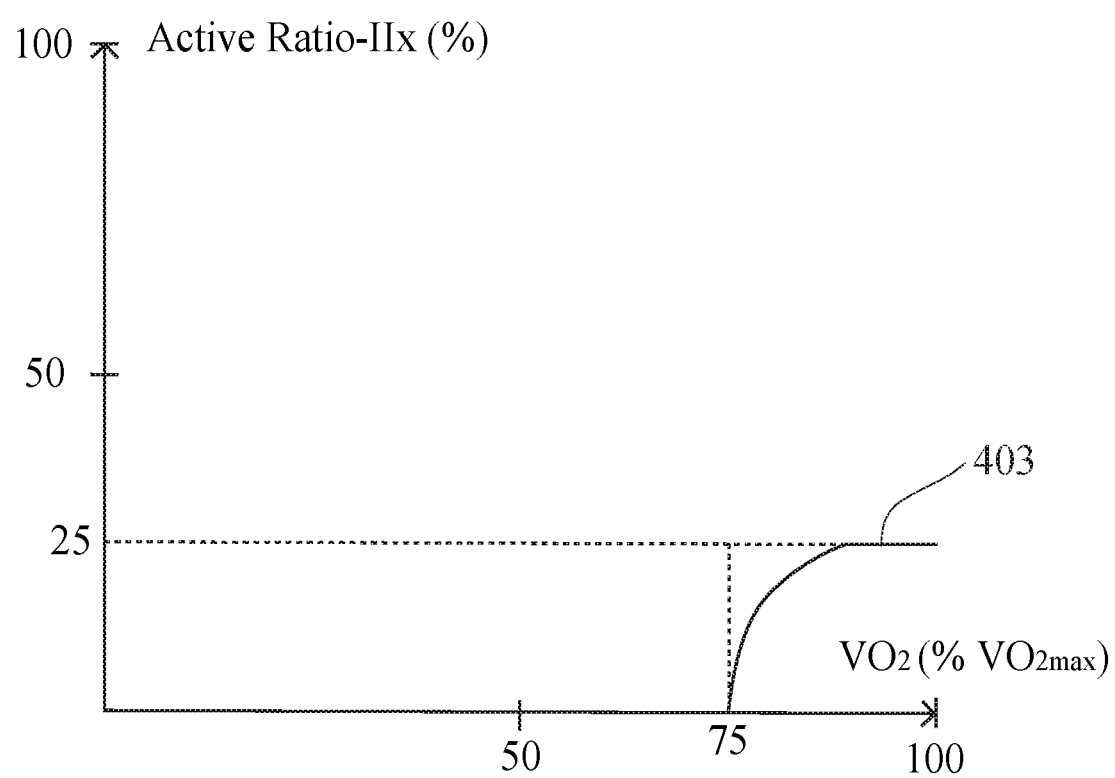
FIG. 4C illustrates the relationship between the degree of active participation AP3 of type IIx muscle fibers and the exercise intensity.

Case I—The feature factor $F_i$ is expressed above the threshold $T_{11}$ of the exercise intensity such that the energy metabolism system 301 is operated above the threshold $T_{11}$ of the exercise intensity:

The feature factor $F_i$ of the energy metabolism feature 303 of the energy metabolism system 301 may be expressed above a threshold $T_{11}$ of the exercise intensity such that the energy metabolism system 301 is operated above the threshold $T_{11}$ of the exercise intensity, thereby monitor the exercise with the exercise intensity more than the threshold $T_{11}$ based on the energy expenditure. Preferably, the threshold $T_{11}$ of the exercise intensity is an anaerobic threshold. The feature factor $F_i$ may be a relationship between a physiological parameter associated with the first biological system and the exercise intensity above the threshold $T_{11}$. The physiological parameter associated with the first biological system may be used for evaluating whether the energy metabolism of the first biological system is thriving or not. The physiological parameter associated with the first biological system may be a degree of active participation associated with the first biological system. The degree of active participation associated with first the biological system may be the degree of active participation of a component of the first biological system. The relationship between the degree of active participation associated with the first biological system and the exercise intensity above the threshold $T_{11}$ may be acquired by performing a process. The property of the cell changes when the cell changes from being inactive to being active. For example, when the muscle cells are electrically or neurologically active, the electric potential generated by the muscle cells can be detected by electromyograph. For example, when the cell changes from being inactive to being active, the glycogen reserve in the cell decreases. Therefore, the process capable of detecting the change can be used to acquire the relationship. For example, FIG. 4A illustrates the relationship 401 between the degree of active participation AP1 of type I muscle fibers and the exercise intensity, FIG. 4B illustrates the relationship 402 between the degree of active participation AP2 of type IIa muscle fibers and the exercise intensity and FIG. 4C illustrates the relationship 403 between the degree of active participation AP3 of type IIx muscle fibers and the exercise intensity. Type I muscle fibers, type IIa muscle fibers and type IIx muscle fibers are called the overall muscle fibers. In FIG. 4A, the parameter of the degree of active participation AP1 of type I muscle fibers is a ratio of the number of active type I muscle fibers to the number of the overall muscle fibers abbreviated as Active Ratio-I and the parameter of the exercise intensity is the oxygen consumption abbreviated as $VO_2$. The unit of Active Ratio-I is % and the unit of $VO_2$ is % $VO_{2max}$. Type I muscle fibers are active above about 0% $VO_{2max}$ (i.e. the relationship 401 is expressed above about 0% $VO_{2max}$) and the maximum of Active Ratio-I is about 35%. In FIG. 4B, the parameter of the degree of active participation AP2 of type IIa muscle fibers is a ratio of the number of active type IIa muscle fibers to the number of the overall muscle fibers abbreviated as Active Ratio-IIa and the parameter of the exercise intensity is the oxygen consumption abbreviated as $VO_2$. The unit of Active Ratio-IIa is % and the unit of $VO_2$ is % $VO_{2max}$. Type IIa muscle fibers are active above about 40% $VO_{2max}$ (i.e. the relationship 402 is expressed above about 40% $VO_{2max}$) and the maximum of Active Ratio-IIa is about 40%. In FIG. 4C, the parameter of the degree of active participation AP3 of type IIx muscle fibers is a ratio of the number of active type IIx muscle fibers to the number of the overall muscle fibers abbreviated as Active Ratio-IIx and the parameter of the exercise intensity is the oxygen consumption abbreviated as $VO_2$. The unit of Active Ratio-IIx is % and the unit of $VO_2$ is % $VO_{2max}$. Type IIx muscle fibers are active above about 75% $VO_{2max}$ (i.e. the relationship 403 is expressed above about 75% $VO_{2max}$) and the maximum of Active Ratio-IIx is about 25%. Preferably, the threshold $T_{11}$ of the exercise intensity is an anaerobic threshold. The anaerobic threshold is about 50%~60% $VO_{2max}$ for the general population. For example, the feature factor $F_1$ of the energy metabolism feature 303 of IIx system is the relationship 403 associated with type IIx muscle fibers expressed above about 75% $VO_{2max}$ such that IIx system is operated above about 75% $VO_{2max}$ (75% $VO_{2max}$ is more than the anaerobic threshold for the general population).

The relationship 401 in FIG. 4A, the relationship 402 in FIG. 4B and the relationship 403 in FIG. 4C are peculiar to and associated with the skeletal muscle system which is one sub-system of the muscular system. However, the relationship 401 in FIG. 4A, the relationship 402 in FIG. 4B and the relationship 403 in FIG. 4C don't exist in any other biological system of the human body.

Case II—The feature factor $S_i$ is expressed above the threshold $T_{12}$ of the exercise intensity more than the threshold $T_{11}$ of the exercise intensity above which the feature factor $F_i$ is expressed such that the energy metabolism system 301 is operated above the threshold $T_{12}$ of the exercise intensity:

The energy metabolism feature 303 further comprises a feature factor $S_i$ expressed above a threshold $T_{12}$ of the exercise intensity more than the threshold $T_{11}$ of the exercise intensity above which the feature factor $F_i$ is expressed, wherein the mathematical model 302 is built up based on the energy metabolism feature 303 comprising a combination of the feature factor $F_i$ and the feature factor $S_i$ for the energy metabolism system 301 such that the energy metabolism system 301 is operated above the threshold $T_{12}$ of the exercise intensity, thereby monitor the exercise with the exercise intensity more than the threshold $T_{12}$ based on the energy expenditure. Preferably, the threshold $T_{12}$ of the exercise intensity is an anaerobic threshold. The feature factor $S_i$ may be associated with the complete human body. The feature factor $S_i$ may be associated with an anaerobic energy metabolism expressed above (about) the anaerobic threshold such that the threshold $T_{12}$ of the exercise intensity is (about) the anaerobic threshold. For example, the feature factor $F_i$ of the energy metabolism feature 303 of the energy metabolism system 301 is the relationship 402 associated with type IIa muscle fibers expressed above about 40% $VO_{2max}$ such that IIa system is operated above about 40% $VO_{2max}$, but 40% $VO_{2max}$ is less than the anaerobic threshold for the general population. In order to make IIa system be operated above the anaerobic threshold, the feature factor $S_i$ associated with the anaerobic energy metabolism may be combined with the feature factor $F_i$ associated with type IIa muscle fibers of the energy metabolism feature 303 of IIa system to create IIa-anaerobic system having an energy metabolism feature 303 comprising a combination of the feature factor $F_i$ associated with type IIa muscle fibers and the feature factor $S_i$ associated with the anaerobic energy metabolism. Build up a mathematical model 302 based on a combination of the feature factor $F_i$ associated with type IIa muscle fibers and the feature factor $S_i$ associated with the anaerobic energy metabolism for IIa-anaerobic system such that IIa-anaerobic system is operated above (about) the anaerobic threshold.

The energy metabolism system 301 in Case I and Case II of the present invention is operated above the threshold $T_1$ of the exercise intensity (the threshold $T_1$ is threshold $T_{11}$ in Case I and the threshold $T_1$ is threshold $T_{12}$ in Case II).

Preferably, the threshold $T_1$ of the exercise intensity is an anaerobic threshold. If the threshold $T_2$ of the exercise intensity (e.g., resting exercise intensity or resting heart rate), above which a predefined energy metabolism system is operated, is less than the threshold $T_1$ of the exercise intensity, above which the energy metabolism system 301 in Case I and Case II of the present invention is operated, and the exercise with the exercise intensity above the threshold $T_1$ can't be precisely monitored based on the energy expenditure estimated by the predefined energy metabolism system (especially the threshold $T_1$ of the exercise intensity is an anaerobic threshold), each of the energy metabolism system 301 in Case I and Case II of the present invention and the predefined energy metabolism system can be used together to precisely monitor the exercise with the exercise intensity above the threshold $T_1$.

In one embodiment, the energy metabolism feature of the predefined energy metabolism system may comprise a feature factor associated with the first biological system and not associated with the complete human body. For example, the energy metabolism system 301 in Case I and Case II of the present invention and the predefined energy metabolism are respectively IIx system and IIa system, or IIa system and I system, or IIx system and I system, or fast-twitch muscle fibers system and slow-twitch muscle fibers system.

For Case I and Case II, the present invention builds up a mathematical model 302 based on the elite biological system of the human body associated with the exercise intensity above the threshold $T_1$ (e.g., anaerobic threshold) for the energy metabolism system 301 (The threshold $T_1$ is threshold $T_{11}$ in Case I and the threshold $T_1$ is threshold $T_{12}$ in Case II); therefore, the present invention can use the limited/the least energy metabolism system(s) (may be only two energy metabolism systems: a predefined energy metabolism and each of the energy metabolism system 301 in Case I and the energy metabolism system 301 in Case II of the present invention) to precisely evaluate the exercise condition with the exercise intensity more than the threshold $T_1$ in the most efficient and the most economical way when facing the complicated human physiological environment above the threshold $T_1$ of the exercise intensity (e.g., anaerobic threshold).

For Case I, specifically speaking, the feature factor $F_i$ is expressed above the threshold $T_{11}$ of the exercise intensity such that the energy metabolism system 301 is capable of being operated above the threshold $T_{11}$ of the exercise intensity without any other feature factor being combined with the feature factor $F_i$ in the energy metabolism feature 303, thereby monitor the exercise with the exercise intensity more than the threshold $T_{11}$ based on the energy expenditure. Preferably, the threshold $T_{11}$ of the exercise intensity is an anaerobic threshold. For example, the feature factor $F_i$ of the energy metabolism feature 303 of IIx system is the relationship 403 associated with type IIx muscle fibers expressed above about 75% $VO_{2max}$ such that IIx system is operated above about 75% $VO_{2max}$ (75% $VO_{2max}$ is more than the anaerobic threshold for the general population). Compared to IIa-anaerobic system in the example of Case II, the feature factor $F_i$ associated with type IIx muscle fibers is expressed above the anaerobic threshold such that IIx system is capable of being operated above the anaerobic threshold without any other feature factor associated with the anaerobic energy metabolism being combined with the feature factor $F_i$ associated with type IIx muscle fibers in the energy metabolism feature 303, which saves computer resource (i.e., save computer resource: the number of the feature factors is less>> the computer program code isn't more complicated>> save more computer resource) and precisely monitor the exercise with the exercise intensity above the anaerobic threshold at the same time.

For Case I, the present invention builds up a mathematical model 302 based on the elite biological system of the human body and the exercise intensity above the threshold $T_I$ (e.g., anaerobic threshold) both existing in the feature factor $F_i$ for the energy metabolism system 301; therefore, the present invention can use the limited/at least feature factor(s) to build up a mathematical model 302 (i.e., save computer resource: the number of the feature factors is less>> the computer program code isn't more complicated>> save more computer resource) in the limited/the least energy metabolism system(s) to precisely evaluate the exercise condition with the exercise intensity more than the threshold $T_{11}$ in the most efficient and the most economical way when facing the complicated human physiological environment above the threshold $T_{11}$ of the exercise intensity (e.g., anaerobic threshold).

The anaerobic threshold is not a constant and varies with many factors coming from the interior of the body or the external environment. No matter how the anaerobic threshold varies with many factors coming from the interior of the body or the external environment, the energy metabolism system 301 (e.g., IIx system) in Case I of the present invention, which must be operated above the anaerobic threshold without any other feature factor being combined with the feature factor $F_i$ in the energy metabolism feature 303 due to the feature factor $F_i$ expressed above the anaerobic threshold, can precisely monitor the exercise with the exercise intensity firmly more than the anaerobic threshold without measuring the anaerobic threshold in advance. It is the most efficient and the most economical way when facing the complicated human physiological environment above the anaerobic threshold. On the contrary, if the threshold, above which the energy metabolism system 301 (e.g., IIa system) is operated, is less than the anaerobic threshold, the energy metabolism system 301 can't identify whether the current exercise intensity is more than the anaerobic threshold or not; therefore, it is defective for the energy metabolism system 301 (e.g., IIa system) to monitor the exercise with the exercise intensity firmly more than the anaerobic threshold.

In step 203: estimating the energy expenditure based on the at least one exercise-associated parameter measured in the exercise by the mathematical model 302 of the energy metabolism system 301 (by the processing unit 102). Once the mathematical model 302 of the energy metabolism system 301 is built up, the energy expenditure may be estimated for the energy metabolism system 301.

Figure 5:
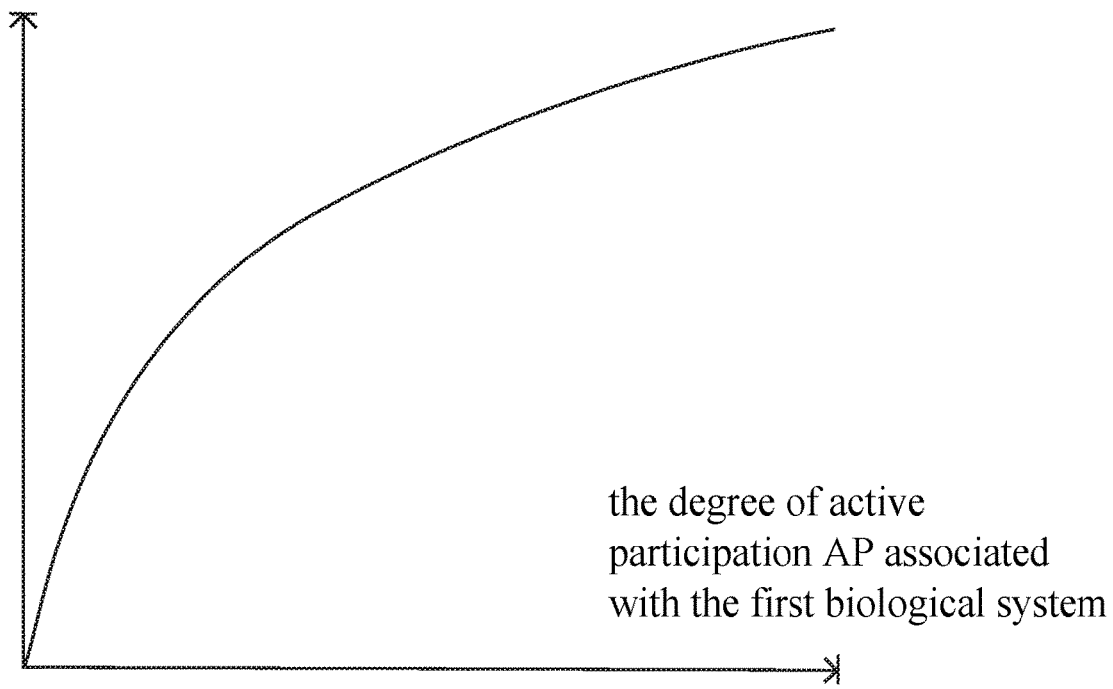
FIG. 5 illustrates the relationship between the ratio Y and the degree of active participation AP associated with the first biological system in one embodiment.

In one embodiment, the feature factor $F_i$ may be a relationship between a physiological parameter associated with the first biological system and the exercise intensity above the threshold $T_{11}$; the physiological parameter associated with the first biological system may be used for evaluating whether the energy metabolism of the first biological system is thriving or not; the process includes: determining the physiological parameter associated with the first biological system based on the exercise intensity measured in the exercise by the relationship; and using at least one exercise-associated parameter and the physiological parameter associated with the first biological system to estimate the energy expenditure by the mathematical model 302 of the energy metabolism system 301. The reference energy expenditure may be determined based on at least one exercise-associated parameter (e.g., exercise intensity); and the energy expenditure may be estimated based on the physiological parameter associated with the first biological system and the reference energy expenditure. The reference energy expenditure may be an additional energy expenditure of the human body resulting from the exercise, so the reference energy expenditure may exclude the basic metabolism energy of the human body. The reference energy expenditure may be determined by any suitable method. For example, if the exercise intensity is presented in the form of the velocity, the reference energy expenditure may be acquired by the formula: the reference energy expenditure=0.5*the mass of the human body*velocity². If the exercise intensity is presented in the form of the energy expenditure rate, the reference energy expenditure may be acquired by the formula: the reference energy expenditure=the energy expenditure rate*exercise time; however, the present invention is not limited to these cases. The energy expenditure may be estimated by the formula: the energy expenditure=the reference energy expenditure*ratio Y; the ratio Y may be adjusted based on the physiological parameter associated with the first biological system, or the ratio Y may be adjusted based on a combination of the physiological parameter associated with the first biological system and any other associated parameter. The relationship between the ratio Y and the physiological parameter associated with the first biological system may be shown in FIG. 5 according to the observation or the result derived from the algorithm, wherein the physiological parameter associated with the first biological system is the degree of active participation AP associated with the first biological system.

Take the physiological parameter associated with the first biological system being the degree of active participation AP3 of type IIx muscle fibers for example; however, the present invention is not limited to this case. The physiological parameter associated with the first biological system being one of the degree of active participation AP2 of type IIa muscle fibers and the degree of active participation AP1 of type I muscle fibers may be also used for an exemplary case. The energy expenditure may be estimated based on the exercise intensity and the degree of active participation AP3 of type IIx muscle fibers (see FIG. 4C) by the formula derived from the mathematical model 302 of IIx system:

Energy Expenditure=function $f_1$ (reference energy expenditure, ratio Y)=the reference energy expenditure*ratio Y;

Ratio Y=function $f_2$ (the degree of active participation AP3 of type IIx muscle fibers) or function $f_2$ (the degree of active participation AP3 of type IIx muscle fibers, any other associated parameter).

The ratio Y may be adjusted based on the degree of active participation AP3 of type IIx muscle fibers, or the ratio Y may be adjusted based on a combination of the degree of active participation AP3 of type IIx muscle fibers and any other associated parameter. The any other associated parameter may be the degree of active participation AP2 of type IIa muscle fibers or the degree of active participation AP1 of type I muscle fibers.

The energy expenditure of IIx system may be estimated as described below.

The energy expenditure may be estimated by taking U.S. application Ser. No. 17/070,040 as a reference. All kinds of method for estimating the energy expenditure in U.S. application Ser. No. 17/070,040 can be incorporated by reference therein.

For example, U.S. application Ser. No. 17/070,040 describes a method for estimating the energy expenditure in the next paragraph.

Use the exercise intensity, the degree of active participation AP1 of type IIa muscle fibers and the degree of active participation AP2 of type I muscle fibers to estimate the first energy expenditure by the mathematical model 503 of the energy metabolism system 501 of type IIa muscle fibers (step 404a). Use the exercise intensity, the degree of active participation AP1 of type IIa muscle fibers and the degree of active participation AP2 of type I muscle fibers to estimate the second energy expenditure by the mathematical model 513 of the energy metabolism system 511 of type I muscle fibers (step 404b). In one embodiment, determine a reference energy expenditure based on the exercise intensity; and estimating the first energy expenditure and the second energy expenditure based on the degree of active participation AP1 of type IIa muscle fibers, the degree of active participation AP2 of type I muscle fibers and the reference energy expenditure. For example, each of the first energy expenditure and the second energy expenditure may be estimated based on a ratio of the degree of active participation AP1 of type IIa muscle fibers to the degree of active participation AP2 of type I muscle fibers. Take a simple example (I), see FIG. 6A and FIG. 6B of U.S. application Ser. No. 17/070,040; when the exercise intensity is 50% $VO_{2max}$, Active Ratio-IIa is about 30%, Active Ratio-I is about 35% (i.e. the maximum of Active Ratio-I) and the ratio of Active Ratio-IIa to Active Ratio-I is 30/35; when the user having a mass of 60 kg runs at the velocity (i.e. the exercise intensity) of 8 m/s, the reference energy expenditure is 1920 J (0.5*60*8²); if the reference energy expenditure is divided into the first energy expenditure and the second energy expenditure based on 30/35 (i.e. the ratio of Active Ratio-IIa to Active Ratio-I), the first energy expenditure is about 886J (1920*30/(30+35)) and the second energy expenditure is about 1034J (1920*35/(30+35)); it should be noted that the present invention is not limited to this case and comprise any other more complicated case.

In step 204: monitoring the exercise based on the energy expenditure (by the processing unit 102). Monitoring the exercise may comprise estimating the exercise-monitoring parameters based on the energy expenditure and displaying words, a voice or an image generated based on the exercise-monitoring parameters to remind the user taking exercise by the output unit 104 of the electronic apparatus 100. Monitoring the exercise may comprise estimating the exercise-monitoring parameters based on the energy expenditure and providing exercise guiding or exercise suggestion for the user taking exercise. The exercise-monitoring parameters may comprise stamina, training load, injury risk, fatigue or recovery.

The exercise-monitoring parameters may be estimated by any suitable method. Take the stamina for example; the stamina may be estimated by taking one of U.S. application Ser. No. 14/718,104 and U.S. application Ser. No. 17/070,040 as a reference. All kinds of method for estimating the stamina in U.S. application Ser. No. 14/718,104 and U.S. application Ser. No. 17/070,040 can be incorporated by reference therein.

For example, U.S. application Ser. No. 17/070,040 describes a method for estimating the stamina in the next paragraph.

The energy metabolism system of type IIa muscle fibers has an energy reserve 5000 J and the energy metabolism system of type I muscle fibers has an energy reserve 10000 J; if the first energy expenditure is about 886 J and the second energy expenditure is about 1034 J by taking example (I) as a reference, the first remaining energy ratio of the energy metabolism system of type IIa muscle fibers is 82.28% (1-886/5000) and the second remaining energy ratio of the energy metabolism system of type I muscle fibers is 89.66% (1-1034/10000); the stamina may be a function of the first remaining energy ratio $R_1$ and the second remaining energy ratio $R_2$, such as $c1*R_1+c2*R_2$ (each of the coefficients c1, c2 is positive, and each of the coefficients c1, c2 may be fixed or variable according to the observation of the physiological phenomenon).

The above disclosure is related to the detailed technical contents and inventive features thereof. People skilled in the art may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A method for monitoring an exercise, comprising:
    building up, by a processing unit, an energy metabolism system having an energy metabolism feature, wherein the energy metabolism feature comprises a first feature factor, wherein the first feature factor is associated with a first biological system being one of a plurality of biological systems of a human body and not associated with the complete human body;
    building up, by the processing unit, a mathematical model describing that an energy expenditure depends on at least one exercise-associated parameter based on the energy metabolism feature for the energy metabolism system;
    estimating, by the processing unit, the energy expenditure based on the at least one exercise-associated parameter measured in the exercise by the mathematical model of the energy metabolism system; and
    monitoring, by the processing unit, the exercise based on the energy expenditure,
    wherein the at least one exercise-associated parameter comprises an exercise intensity, the first feature factor is expressed above a first threshold of the exercise intensity such that the energy metabolism system is operated above the first threshold of the exercise intensity, thereby monitoring the exercise with the exercise intensity higher than the first threshold based on the energy expenditure,
    wherein the first threshold of the exercise intensity is an anaerobic threshold, the exercise intensity is measured by a sensor, and wherein the sensor is selected from a group consisting of heart rate sensor, accelerometer, magnetometer, gyroscope, and position sensor.

2. The method according to claim 1, wherein the first biological system is an exercise-responsive system having a degree of exercise response higher than a threshold, wherein the threshold is higher than a minimum of the degree of exercise response.

3. The method according to claim 2, wherein a parameter of the degree of exercise response is a ratio of a first blood flow rate in the heavy exercise to a second blood flow rate at rest, wherein the threshold is 1.1.

4. The method according to claim 1, wherein the exercise-responsive system is a muscular system.

5. The method according to claim 4, wherein the exercise-responsive system is a skeletal muscle system.

6. The method according to claim 1, wherein the first feature factor is a relationship between a physiological parameter associated with the first biological system and the exercise intensity above the first threshold, wherein the physiological parameter associated with the first biological system is used for evaluating whether an energy metabolism of the first biological system is thriving or not.

7. The method according to claim 6, wherein the physiological parameter associated with the first biological system is a degree of active participation associated with the first biological system.

8. The method according to claim 6, wherein the physiological parameter associated with the first biological system is determined based on the exercise intensity measured in the exercise by the relationship, wherein the energy expenditure is estimated further based on the physiological parameter associated with the first biological system by the mathematical model of the energy metabolism system.

9. The method according to claim 1, wherein the first feature factor is expressed above the first threshold of the exercise intensity such that the energy metabolism system is capable of being operated above the first threshold of the exercise intensity without a second feature factor being combined with the first feature factor in the energy metabolism feature, thereby monitoring the exercise with the exercise intensity higher than the first threshold based on the energy expenditure.

10. The method according to claim 9, wherein the first threshold of the exercise intensity is an anaerobic threshold.

11. The method according to claim 1, wherein the energy metabolism feature further comprises a second feature factor expressed above a second threshold of the exercise intensity higher than the first threshold of the exercise intensity, wherein the mathematical model is built up based on the energy metabolism feature comprising a combination of the first feature factor and the second feature factor for the energy metabolism system such that the energy metabolism system is operated above the second threshold of the exercise intensity, thereby monitoring the exercise with the exercise intensity higher than the second threshold based on the energy expenditure.

12. The method according to claim 11, wherein the second threshold of the exercise intensity is an anaerobic threshold.

13. The method according to claim 12, wherein the second feature factor is associated with an anaerobic energy metabolism expressed above the anaerobic threshold such that the second threshold of the exercise intensity is the anaerobic threshold.

14. A method for monitoring an exercise, comprising:
    building up, by a processing unit, a first energy metabolism system having an first energy metabolism feature, wherein the first energy metabolism system is operated above a first threshold of an exercise intensity, wherein the first energy metabolism feature comprises a first feature factor, wherein the first feature factor is associated with a first biological system being one of a plurality of biological systems of a human body and not associated with the complete human body;
    building up, by the processing unit, a first mathematical model describing that a first energy expenditure depends on at least one exercise-associated parameter based on the first energy metabolism feature for the first energy metabolism system;
    building up, by the processing unit, a second energy metabolism system having an second energy metabolism feature, wherein the second energy metabolism system is operated above a second threshold of the exercise intensity, wherein the first threshold of the exercise intensity is larger than the second threshold of the exercise intensity;

building up, by the processing unit, a second mathematical model describing that a second energy expenditure depends on the at least one exercise-associated parameter based on the second energy metabolism feature for the second energy metabolism system;

estimating, by the processing unit, the first energy expenditure and the second energy expenditure based on the at least one exercise-associated parameter measured in the exercise respectively by the first mathematical model of the first energy metabolism system and the second mathematical model of the first energy metabolism system; and monitoring, by the processing unit, the exercise based on the first energy expenditure and the second energy expenditure, wherein the first threshold of the exercise intensity is an anaerobic threshold, the exercise intensity is measured by a sensor, and wherein the sensor is selected from a group consisting of heart rate sensor, accelerometer, magnetometer, gyroscope, and position sensor.

15. The method according to claim 14, wherein the second energy metabolism feature comprises a second feature factor, and the second feature factor is associated with the first biological system and not associated with the complete human body.

16. A method for monitoring an exercise, comprising:

building up, by a processing unit, an energy metabolism system having an energy metabolism feature, wherein the energy metabolism feature comprises a first feature factor, wherein the first feature factor is associated with a first biological system being one of a plurality of biological systems of a human body and not associated with the complete human body, wherein the first biological system is an exercise-responsive system having a ratio of a first blood flow rate in the heavy exercise to a second blood rate flow at rest, wherein the ratio is higher than 3, wherein the first feature factor is expressed above an anaerobic threshold such that the energy metabolism system is capable of being operated above the anaerobic threshold without a second feature factor being combined with the first feature factor in the energy metabolism feature;

building up, by the processing unit, a mathematical model describing that an energy expenditure depends on at least one exercise-associated parameter based on the energy metabolism feature for the energy metabolism system;

estimating, by the processing unit, the energy expenditure based on the at least one exercise-associated parameter measured in the exercise by the mathematical model of the energy metabolism system, wherein the at least one exercise-associated parameter comprises an exercise intensity measured by a sensor, and wherein the sensor is selected from a group consisting of heart rate sensor, accelerometer, magnetometer, gyroscope, and position sensor; and monitoring, by the processing unit, the exercise based on the energy expenditure.

17. The method according to claim 16, wherein the first biological system is a skeletal muscle system, and the first feature factor is a relationship between a degree of active participation associated with the skeletal muscle system and the exercise intensity above the anaerobic threshold, wherein the degree of active participation associated with the skeletal muscle system is determined based on the exercise intensity measured in the exercise by the relationship, and the energy expenditure is estimated further based on the degree of active participation associated with the skeletal muscle system by the mathematical model of the energy metabolism system.

18. The method according to claim 17, wherein the degree of active participation associated with the skeletal muscle system is the degree of active participation of type IIx muscle fibers.

* * * * *